US006239593B1

(12) United States Patent
Burkhardt et al.

(10) Patent No.: US 6,239,593 B1
(45) Date of Patent: May 29, 2001

(54) METHOD AND SYSTEM FOR DETECTING AND CHARACTERIZING MECHANICAL DAMAGE IN PIPELINES USING NONLINEAR HARMONICS TECHNIQUES

(75) Inventors: Gary L. Burkhardt, Adkins; Alfred E. Crouch, San Antonio, both of TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/157,646

(22) Filed: Sep. 21, 1998

(51) Int. Cl.[7] .......................... G01N 27/72; G01R 33/12; G01R 33/18; G01B 7/24
(52) U.S. Cl. .......................... 324/233; 324/220; 324/225; 324/209; 702/38
(58) Field of Search .................................. 324/233, 219, 324/220, 221, 234, 237, 238, 239, 240, 242, 225, 209; 702/38, 72

(56) References Cited

U.S. PATENT DOCUMENTS

| 4,909,091 | * | 3/1990 | Ellmann et al. ..................... 324/220 |
| 5,144,565 | * | 9/1992 | Brown et al. ......................... 702/38 |

OTHER PUBLICATIONS

R. J. Davis et al., "The Feasibility of Magnetic Flux Leakage In-Line Inspection as a Method to Detect and Characterize Mechanical Damage", Southwest Research Institute Report, Jun. 1996.

A. E. Crouch, "In-Line Inspection of Natural Gas Pipelines", Southwest Research Institute Report, May 1993.

H. Kwun et al., "Electromagnetic Techniques for Residual Stress Measurements", Metals Handbook, 9th Edition, vol. 17, Nondestructive Evaluation and Quality Control (ASM International, 1989) pp. 159–162.

H. Kwun et al., Nondestructive Measurement of Stress in Ferromagnetic Steels Using Harmonic Analysis of Induced Voltage, NDT International vol. 20 No. 3, Jun. 1987 pp. 167–171.

* cited by examiner

*Primary Examiner*—Walter E. Snow
(74) *Attorney, Agent, or Firm*—Taylor Russell & Russell, P.C.

(57) ABSTRACT

A nondestructive method for inspecting steel pipelines for plastically deformed regions caused by mechanical damage to the pipeline. The invention is a method and system that uses nonlinear harmonic detection methods to detect mechanical damage in pipelines. The invention uses a time-varying magnetic field to sense magnetic properties of the pipeline. The odd-numbered harmonic frequencies are detected and their amplitudes are related to the magnetic condition of the material under test to determine areas of mechanical damage. This technique can be used for rapidly surveying stress states in pipelines where nonlinear harmonic sensing devices are attached to a pigging device moving through a pipeline at a relatively high rate of speed.

34 Claims, 16 Drawing Sheets

METHOD AND SYSTEM FOR DETECTING AND CHARACTERIZING MECHANICAL DAMAGE IN PIPELINES USING NONLINEAR HARMONICS TECHNIQUES

BACKGROUND

The invention relates generally to nondestructive methods for inspecting steel pipelines for plastically deformed regions caused by mechanical damage to the pipeline. More particularly, the invention is a method and system that uses nonlinear harmonic detection methods to detect mechanical damage in pipelines. The invention uses a time-varying magnetic field to sense magnetic properties of the pipeline. The odd-numbered harmonic frequencies are detected and their amplitudes are related to the magnetic condition of the material under test to determine mechanical damage.

Detection and characterization of plastically deformed regions caused by mechanical damage in pipelines, particularly gas transmission pipelines is important because of the danger to pipeline integrity posed by this type of defect. A plastically deformed region is a region in a metal that has been strained beyond the elastic limit and is now permanently deformed. The detection of this type of mechanical damage becomes even more critical because most of the reportable incidents of problems related to defects on operating pipelines are caused by third party contact with the pipeline that results in mechanical damage. Mechanical damage can be in the form of dents or gouges, or both.

Residual stresses and plastic deformation indicating mechanical damage in materials can be nondestructively measured by a variety of methods, including x-ray diffraction, ultrasonic and electromagnetic techniques. Because of the limited penetration depth of x-rays in metals, x-ray diffraction is restricted to measurements of surface stresses, generally in a laboratory environment. Ultrasonic techniques measure the velocity of ultrasonic waves in the metal and relate those measurements to stress. However, there are difficulties in differentiating stress effects from the texture of the material. With electromagnetic techniques, one or more of the magnetic properties (such as permeability, magnetostriction, hysteresis, coercive force, or magnetic domain wall motion during magnetization) of a ferromagnetic material are sensed and correlated to stress. These techniques rely on detecting the change in magnetic properties of the material caused by stress which is known as the magnetoelastic effect. Many of these techniques are difficult to implement without a controlled sample available while the measurement is being done. In addition, these techniques are less sensitive to changes in the magnetic properties of ferromagnetic materials caused by stress than nonlinear harmonics techniques. They are also not generally appropriate for rapidly survey stress states within pipelines, especially when the pipeline is being tested with a pigging device moving through the pipeline at a relatively high rate of speed.

SUMMARY

The present invention detects mechanical damage in ferromagnetic material using nonlinear harmonics (NLH) electromagnetic techniques. The NLH method is applicable to mechanical damage detection because it is sensitive to the changes in magnetic properties of the steel caused by stress and plastic deformation associated with mechanical damage to pipelines. The method and system of the present invention uses nonlinear harmonics techniques to detect and characterize mechanical damage in pipelines. The nonlinear harmonics approach uses a time varying magnetic field to sense the magnetic properties (i.e. permeability) of a component. This method is based on applying an alternating sinusoidal magnetic field at a given excitation frequency. The frequency used may be typically about 10 kHz, but the excitation frequency can range between about 100 Hz to about 100 kHz. Because of magnetic hysteresis and nonlinear permeability of ferromagnetic material, the magnetic induction in the material becomes distorted. The distorted magnetic induction waveform contains odd numbered harmonic frequencies of the applied magnetic field. With the nonlinear harmonics method, one or more of these harmonic frequencies are detected and their amplitudes are related to the magnetic properties of the material under test. Because of the magnetoelastic affect, stress and plastic deformation affect the magnetic properties and thus the harmonic signals. Areas of mechanical damage are then identified and characterized by the NLH response. This technique can be used for rapidly surveying stress states in pipelines where the NLH sensors are attached to a pigging device moving through a pipeline at a relatively high rate of speed (about 10 m/s, or 30 ft/s).

The present invention comprises a system for nondestructive testing utilizing nonlinear harmonics techniques to determine mechanical damage within the ferromagnetic material of a pipeline, comprising a means for supplying a time varying current at a fundamental frequency to a nonlinear harmonic sensor and for outputting a phase reference signal contained within a pigging device for passing through a pipeline, means for amplifying and selecting a portion of the signal that represents a harmonic frequency component of the signal and generating an output signal using the phase reference signal, means connected to the pigging device for converting the output signal to a digital harmonic signal; means connected to the pigging device for storing the digital harmonic signal, and computer means for analyzing the digital harmonic signal to detect areas of mechanical damage within the pipeline. The nonlinear harmonic sensor attached to a pigging device for passage through a pipeline comprises an excitation coil for generating a magnetic field within a pipeline when supplied with the time varying current as the pigging device passes through the pipeline and a sensing coil for detecting a signal caused by induced magnetic field in the pipeline. The computer means for analyzing the digital harmonic signal may be contained within the pigging device. In the preferred embodiment, the computer means for analyzing the digital harmonic signal is external to the pigging device. In the preferred embodiment, the harmonic signal is at a third harmonic frequency of the fundamental frequency. The means for supplying the time varying current at the fundamental frequency to a nonlinear harmonic sensor and for outputting the phase reference signal may be a signal generator and power amplifier.

The digital harmonic signal stored for analysis comprises an in-phase signal component and a quadrature signal component. The phase reference signal component is output to an amplifier which generates an in-phase and quadrature reference signal component. The fundamental frequency may be a selected frequency in the range of between about 100 Hz to about 100 kHz.

A means for amplifying and selecting the portion of the signal that represents the harmonic frequency component of the signal and generating a harmonic signal using the phase reference signal further comprises a filter means for filtering the output signal to remove frequencies other than harmonic frequencies and means for frequency multiplying the phase reference signal and passing the multiplied phase reference signal to a lock-in amplifier that uses the multiplied phase reference signal and filtered harmonic signal to generate a complex harmonic signal with in-phase and quadrature signal components.

The pigging device may comprise a pressure vessel and the nonlinear harmonic sensor may comprise a plurality of nonlinear harmonics sensing devices attached to the pressure vessel to form sensor arrays. The nonlinear harmonics sensing devices may extend outward from spring-loaded suspensions attached to the pressure vessel and the sensing devices may rest against the inner surface of the pipeline. The nonlinear harmonic sensors may be attached to the pressure vessel and oriented with the magnetization direction parallel with a pipeline axis or may be oriented with the magnetization direction perpendicular to a pipeline axis. The pigging device may be capable of traveling through the pipeline at a speed of about ten meters per second.

The present invention comprises a method of nondestructive testing utilizing nonlinear harmonics techniques to determine mechanical damage within ferromagnetic material of a pipeline, comprising the steps of: supplying a time varying current at a fundamental frequency to an excitation coil for generating a magnetic field within a pipeline and outputting a fundamental phase reference signal, within a pigging device for passing through a pipeline; detecting a signal caused by induced magnetic field in the pipeline using a sensing coil attached to the pigging device; amplifying and selecting a portion of the signal that represents a harmonic frequency component of the signal and outputting an output signal; converting the output signal to a digital harmonic signal; storing the digital harmonic signal and phase reference signal within the pigging device; and analyzing the amplitude of the digital harmonic signal to detect areas of mechanical damage within the pipeline using a computer program. The digital harmonic signal stored for analysis comprises an in-phase signal component and a quadrature signal component. The phase reference signal component is output to an amplifier which generates an in-phase and quadrature fundamental signal component.

In an alternate method, a plurality of fundamental frequencies are supplied and the amplitudes of the digital harmonic signals at the plurality of harmonic frequencies are compared to detect areas of mechanical damage within the pipeline.

The method of amplifying and selecting may further comprise filtering the output signal to remove frequencies other than harmonic frequencies and frequency multiplying the phase reference signal and passing the multiplied phase reference signal to a lock-in amplifier that uses the multiplied phase reference signal and filtered harmonic signal to generate a complex harmonic signal with in-phase and quadrature signal components. The method of analyzing the harmonic signal amplitude to detect areas of mechanical damage within the pipeline using a computer program step may further comprise analyzing the amplitude of the signal in-phase and quadrature digital harmonic signal components which contain background signal components, mechanical damage signal components and probe liftoff signal components, determining the amount to phase shift the in-phase and quadrature digital harmonic signal components to remove the background signal and liftoff signal components, and phase shifting the in-phase and quadrature signal components by a selected number of degrees to remove the background signal and liftoff signal components with the resulting signal indicating the areas of mechanical damage along the pipeline. The step of analyzing the harmonic signal amplitude to detect areas of mechanical damage within the pipeline using a computer program may further comprise determining the amount to phase shift the in-phase and quadrature digital harmonic signal components to remove the background signal and liftoff signal components, phase shifting the in-phase and quadrature signal components by a selected number of degrees to remove the background signal and liftoff signal components, comparing the amplitude of the in-phase and quadrature digital harmonic signal components to an amplitude of a threshold signal level and characterizing the amount of mechanical damage using a calibration curve, if the amplitude of the in-phase and quadrature digital harmonic signal is greater than the amplitude of the threshold level. The threshold level signal may be constructed using a specimen that is the same material as the pipeline, placing a nonlinear harmonics sensing device on the specimen, supplying a time varying current at a given frequency to the nonlinear harmonics sensing device and outputting a fundamental phase reference signal, detecting a signal caused by induced magnetic field in the specimen, amplifying and selecting a portion of the signal that represents a harmonic frequency component of the signal and generating an output signal, converting the output signal to a digital harmonic signal, applying a known amount of stress and plastic deformation to the specimen and repeating the above steps for a fixed number of known stresses, constructing the calibration curve by plotting the digital harmonic signal corresponding to each known stress and then constructing a threshold signal level.

In an alternate method, the threshold level signal may be determined using a specimen that is the same material as the pipeline with known amounts of mechanical damage, placing a nonlinear harmonics sensing device on the specimen, supplying a time varying current at a given frequency to the nonlinear harmonics sensing device and outputting a fundamental phase reference signal, detecting a signal caused by induced magnetic field in the specimen; amplifying and selecting a portion of the signal that represents a harmonic frequency component of the signal and generating an output signal, converting the output signal to a digital harmonic signal; constructing the calibration curve by plotting the digital harmonic signal corresponding to the mechanical damage, and constructing a threshold signal level. The number of degrees of phase shifting may be determined by using an optimization software program which phase shifts the signal in incremental amounts to determine a largest amplitude for a signal of interest and a smallest amplitude for a signal not of interest.

In an alternate method, analyzing the amplitude of the digital harmonic signal to detect areas of mechanical damage within the pipeline using a computer program, may comprise using the amplitude of the digital harmonic signal in-phase signal components which contain background signal components, mechanical damage signal components and probe liftoff signal components and using the amplitude of the fundamental in-phase signal components. The digital harmonics signal is scaled to the fundamental in-phase signal, for each area of interest, by taking the reduction in amplitude of the fundamental in-phase signal divided by the reduction in amplitude for the digital harmonic signal, multiplied by the digital harmonic signal amplitude, then subtracting that result from the fundamental in-phase signal amplitude to generate a resulting signal. The resulting signal has substantially all the liftoff signal components removed and substantially all the mechanical damage signal components retained such that areas of mechanical damage along the pipeline are indicated by changes in amplitude of the resulting signal. An alternate method for analyzing the harmonic signal amplitude to detect areas of mechanical damage within the pipeline using a computer program, further comprises calculating anisotropy in the digital harmonic signal amplitude to detect areas of mechanical damage.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1C:
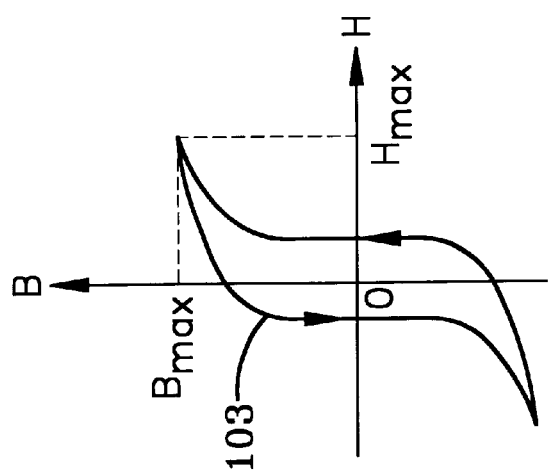
FIGS. 1A, 1B and 1C show the distortion of magnetic induction in a ferromagnetic material caused by hysteresis and nonlinearity.
Figure 1B:
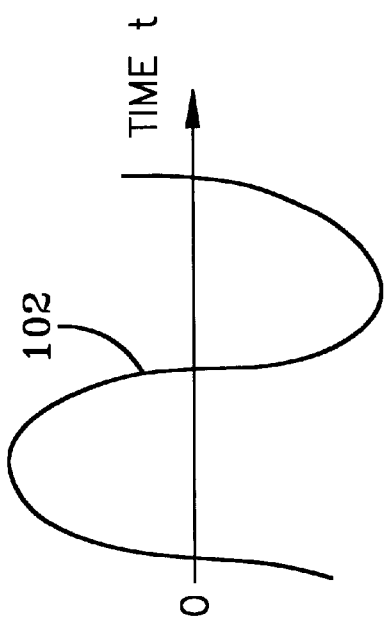
Figure 1A:
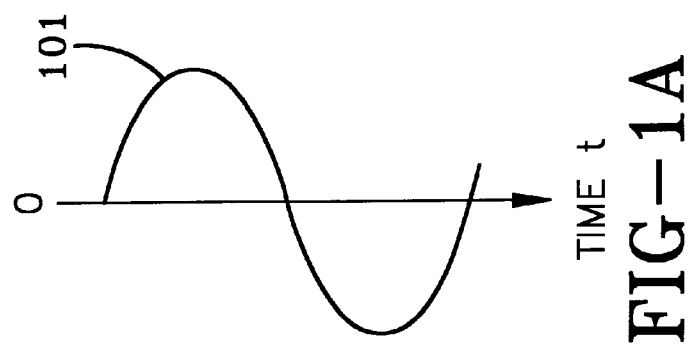

Turning now to FIGS. 1A, 1B and 1C, the distortion of magnetic induction in a ferromagnetic material caused by hysteresis and nonlinearity is shown. When a sinusoidal external magnetic field H, 101 in FIG. 1A is applied to a ferromagnetic material, the resulting magnetic induction, B 102 in FIG. 1B is not sinusoidal but distorted because of the magnetic hysteresis and nonlinear permeability of the material which is shown in FIG. 1C. This distorted waveform 102 of the magnetic induction, or equivalently the voltage induced in a coil by the magnetic induction, contains odd harmonic frequencies of the applied magnetic field. The amount of harmonic component depends on the shape of the hysteresis loop 103 (FIG. 1C). It is known that the shape of the hysteresis loop 103 changes as the stress changes.

Figure 2:
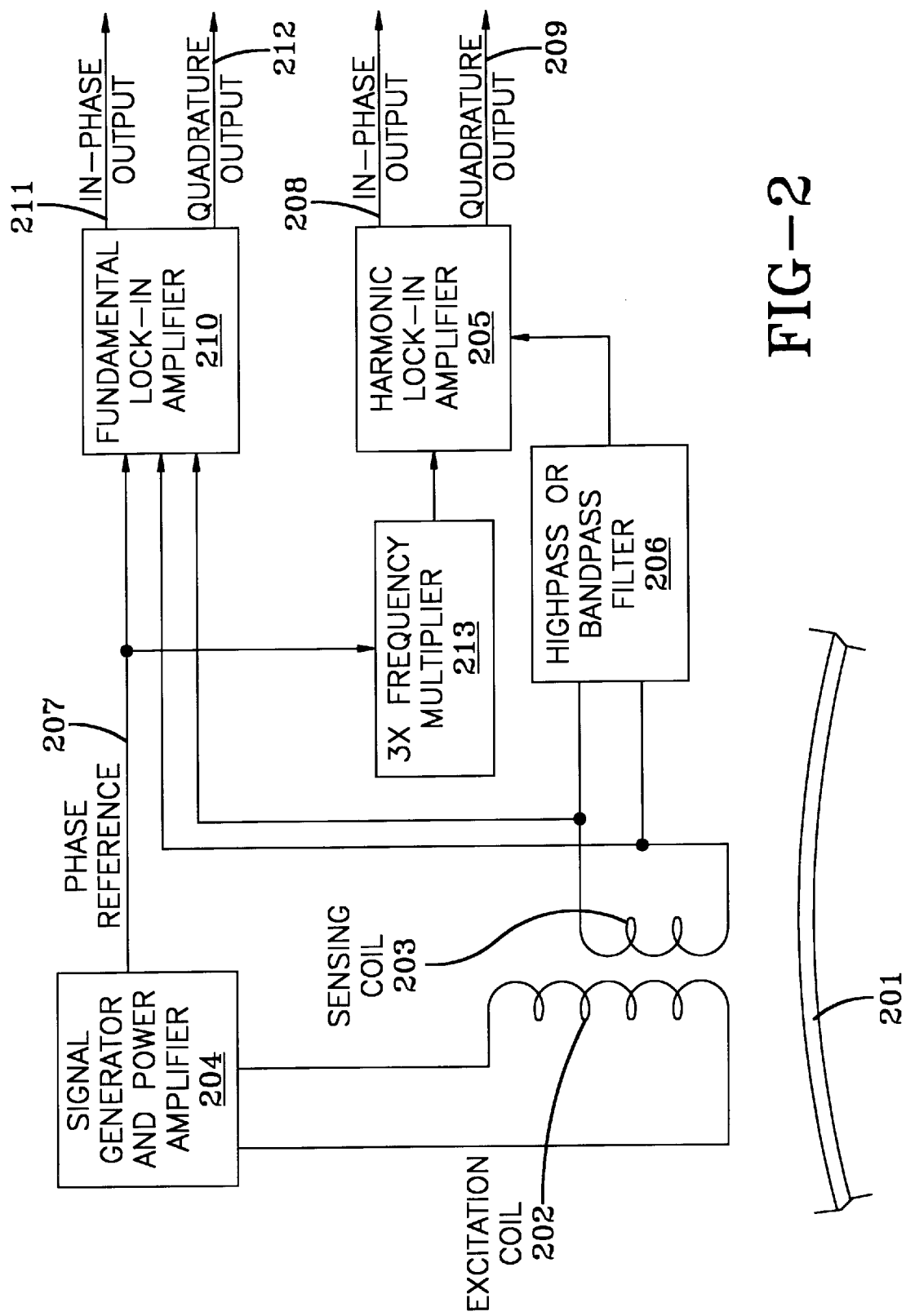
FIG. 2 shows a block diagram of a nonlinear harmonics (NLH) sensing system used on a pipe in accordance with the present inventive concept.
Figure 11:
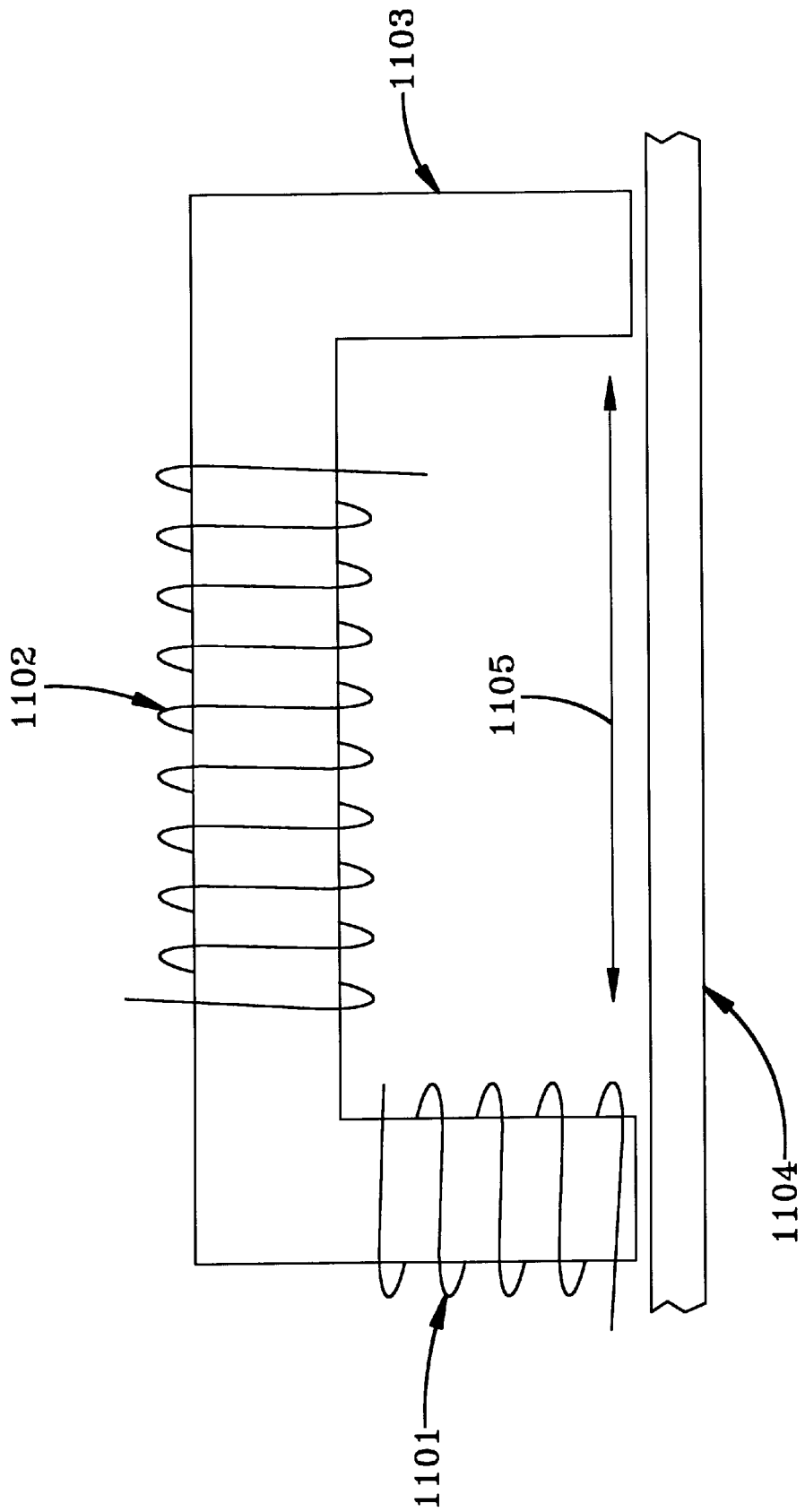
FIG. 11 shows a typical NLH sensor probe configuration in accordance with the present inventive concept.

The nonlinear harmonics techniques may be implemented with the arrangement shown in FIG. 2. FIG. 2 is a block diagram of a nonlinear harmonics (NLH) sensing system used on a pipe. The magnetic field is applied to the pipe wall 201 by an excitation coil 202. In the present invention, the magnetic field is applied to the interior of the pipe wall. The resulting magnetic induction is measured with a magnetic field sensor such as a sensing coil 203. A sinusoidal current of a given frequency is supplied to the excitation coil 202 using a signal generator and power amplifier 204. The induced voltage in the sensing coil 203, is amplified and the harmonic frequency component, typically the third harmonic, is determined using a spectrum analyzer or harmonic lock-in amplifier 205 referenced to the driving waveform. A typical NLH sensor probe configuration is shown in FIG. 11. The phase reference signal 207 is passed through a frequency multiplier 213 that multiplies the fundamental or excitation frequency (in this case by three) and passes it to the harmonic lock-in amplifier 205. The induced voltage in the sensing coil is also output to the fundamental lock-in amplifier 210. A phase reference signal 207 is sent from the signal generator and power amplifier 204 to the fundamental lock-in amplifier 210. Prior to being passed to the harmonic lock-in amplifier 205, the sensor output may be passed through a high pass or bandpass filter 206 to reduce the fundamental component. Simpler configurations such as bandpass filtering the harmonic frequency and detecting the output could also be used. Two orthogonal signal outputs, an in-phase output 208 and a quadrature output 209 are output from the harmonic lock-in amplifier 205. A fundamental in-phase signal output 211 and a fundamental quadrature signal output 212 are output from the fundamental lock-in amplifier 210. The induced voltage in the sensing coil 203 contains odd numbered harmonics, with the third harmonic frequency having the highest amplitude among the harmonics. In general, the amplitude of harmonics higher than the third are quite small. Therefore, generally the amplitude of the third harmonic frequency is used to determine the stress in ferromagnetic material by measuring the stress-related changes in the magnetic material, however other harmonic frequencies may also be used. The arrangement in FIG. 2, consisting of a plurality of excitation coils and sensing coils, may be mounted externally on a pigging device capable of traveling through a pipeline in an axial direction, as shown in FIG. 3.

Figure 3:
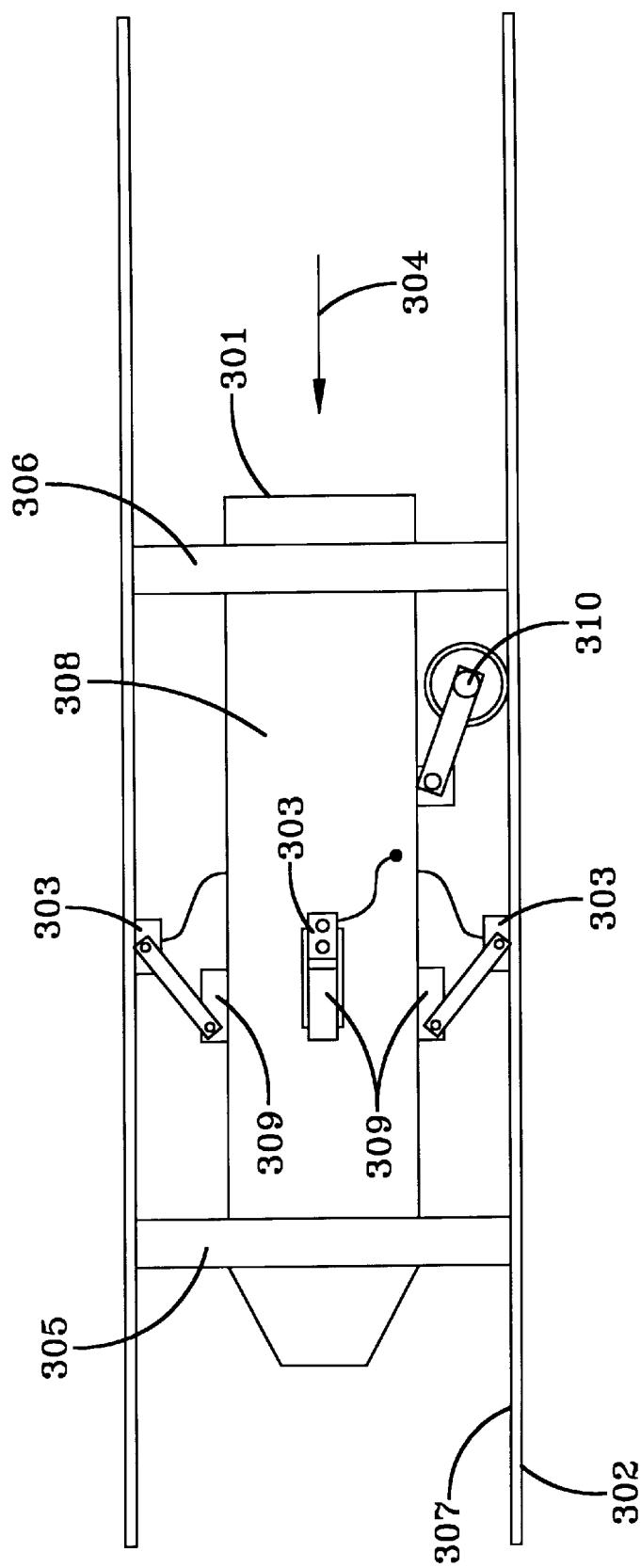
FIG. 3 shows a schematic representation of a pig system for performing a mechanical damage inspection of a pipeline by the using NLH sensors of FIG. 2 in accordance with the present inventive concept.

FIG. 3 shows a schematic representation of a pig system 301 for performing a mechanical damage inspection of a pipeline 302 by the using NLH sensors. Most pipeline inspections are performed from inside the pipeline 302 using free-swimming vehicles called pigs 301. Pigs act like pistons in a pipeline 302, being propelled in the direction of the flow of the transported product 304 by the pressure drop across sealing cups (a front propulsion cup 305 and a rear sealing and centering cup 306) attached to the pig and closely fitting to the pipeline's internal surface 307. The pig includes a pressure vessel or housing 308 that contains all the electronic instrumentation and power sources for the inspection operation. Sensors external to the pig housing 308 feed signals to the electronic instrumentation through electrical feed-throughs (connectors) in the wall of the pressure vessel 308. Data from the sensors are conditioned and recorded by onboard electronics in the pig 301 and then retrieved for analysis after the pig 301 has been removed from the pipeline 302. The pig system 301 uses NLH sensors which may be of a type similar to that shown in FIG. 11. In FIG. 3, a plurality of NLH sensors form sensor arrays 303 and are attached to the outside of the pressure vessel 308. In FIG. 3, three NLH sensors 303 are shown but more sensors may be included but are not shown. The array 303 can contain many sensors (for example, fifty to one-hundred) as required to completely cover the inner surface of the pipe. The NLH sensors 303 extend from spring-loaded suspensions 309 attached to the pressure vessel 308 to rest against the inner surface of the pipeline 307. The NLH sensors can be oriented in axial or transverse directions with respect to the pipeline axis 302. The odometer wheel 310 provides data of axial position in the pipeline 302. These data are recorded along with the NLH sensor outputs. In typical operation, the inspection pig 301 is placed into a pipeline 302 to move with the product flow 304 for fifty to one hundred miles to a retrieval point. Data are then recovered from the onboard storage. The data are then checked for validity and shipped to the inspection headquarters location for analysis. Any serious pipeline defects identified are examined in the field by uncovering the pipeline The precise location of the defect can be determined from correlation with the odometer data.

Figure 4:
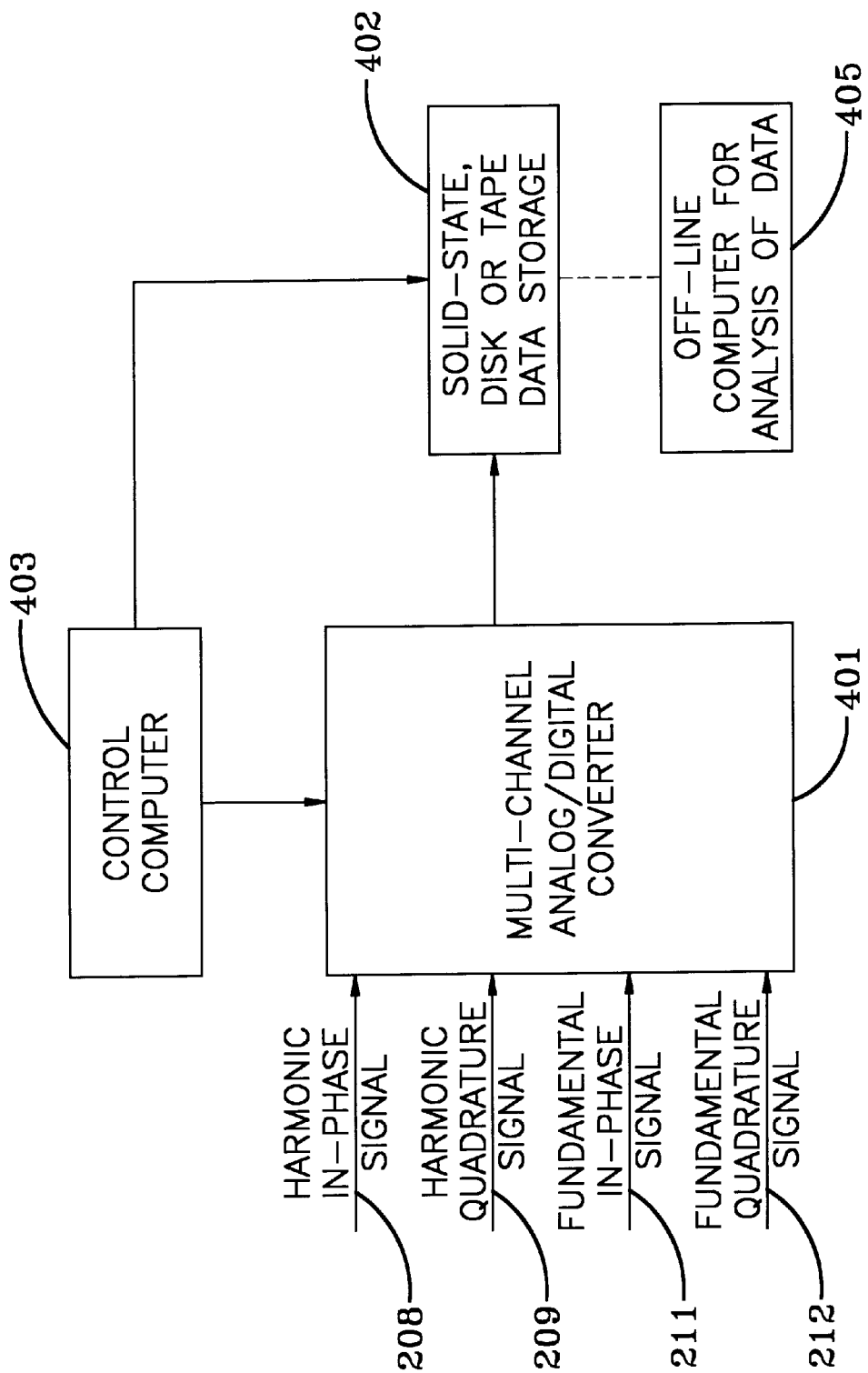
FIG. 4 shows a block diagram of the electronics within the pressure vessel of the inspection pig as depicted FIG. 3 in accordance with the present inventive concept.

A block diagram of the electronics within the pressure vessel 308 of the inspection pig 301 is shown in FIG. 4. A control computer 403 is contained within the pressure vessel. The harmonic and fundamental in-phase and quadrature signal outputs 208, 209, 211 and 212 are fed first to a multi-channel analog digital converter 401. After conversion, it is recorded on a data storage device 402, such as a solid state, disk or tape data storage device. It is then retrieved for analysis after the pig has been removed from the pipeline. This data input, conversion and storage is controlled by the pig's onboard control computer 403. After the data has been recorded on a data storage device 402, the harmonic and fundamental data is analyzed using a computer off-line 405 to determine the areas of mechanical damage in the pipeline. Alternatively, the analysis may be performed within the electronics of the pressure vessel 308 by the control computer 403.

Figure 5:
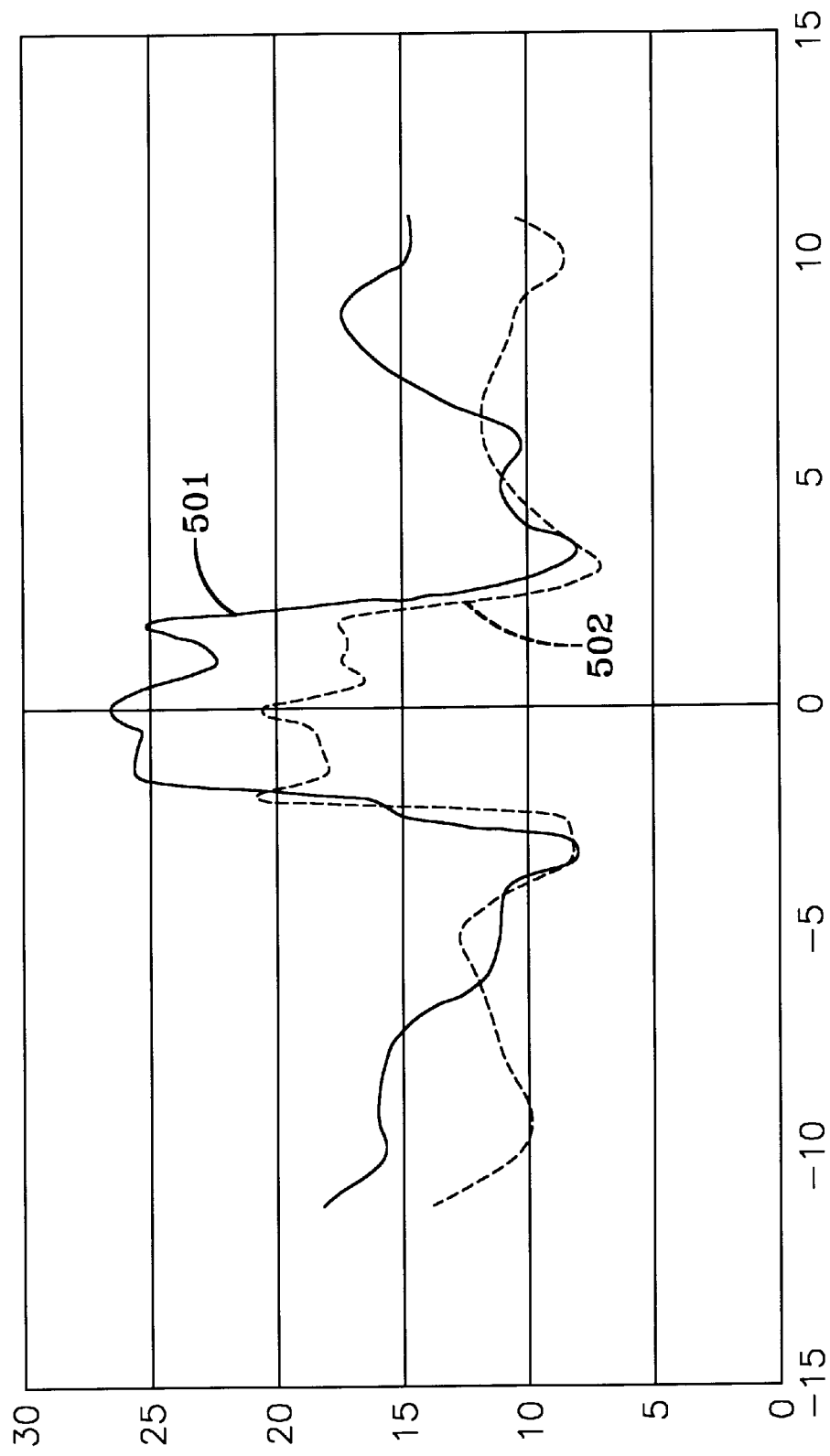
FIG. 5 shows nonlinear harmonics data taken from a mechanically damaged specimen.

FIG. 5 shows nonlinear harmonics data taken from a mechanically damaged specimen. In the pipe wall, the magnetic properties of regions around dents and gouges change because of deformations and stresses associated with the dents and gouges. Those regions will produce an NLH response different from that of the undisturbed material. FIG. 5 shows the NLH response to a mechanical damage defect, in this case a gouge in the pipe wall. FIG. 5 shows a combination of data taken with the coils inducing magnetizing field placed in two directions, parallel or axial 501 and perpendicular 502 in relation to the pipeline wail. Both the axial 501 and the perpendicular 502 components show an increase in the NLH response in the gouged area and in the area immediately surrounding the damaged region.

Figure 6:
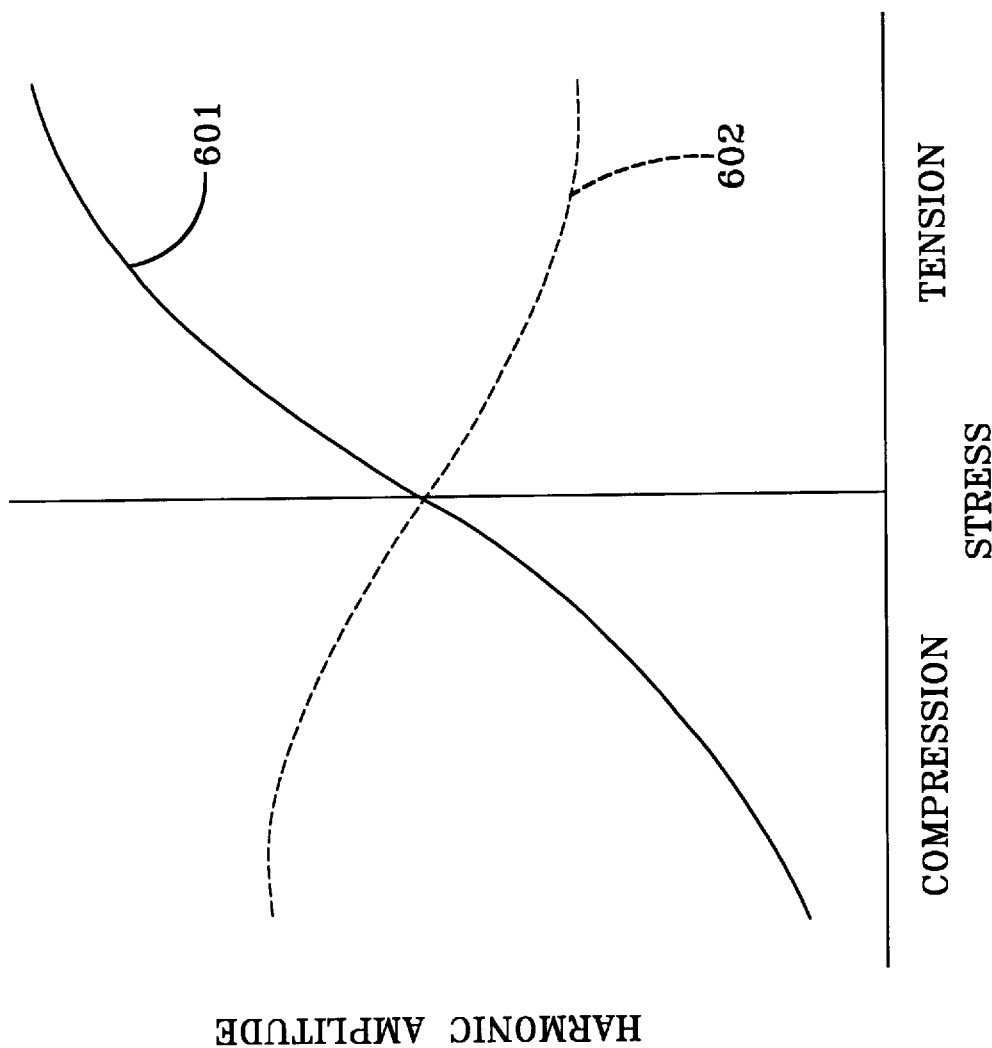
FIG. 6 shows the stress dependence of harmonic amplitude for materials with positive magnetostriction.

The harmonic amplitudes are dependent on the stress as well as the relative orientation between the stress and the applied magnetic field directions. FIG. 6 shows the stress dependence of harmonic amplitude for materials with positive magnetostriction. FIG. 6 shows that the harmonic amplitude for materials with a positive magnetostriction increases with tension when the direction of the stress and the applied fields are parallel. As shown in FIG. 6, when the coils were aligned parallel (line 601) to the stress direction, the harmonic amplitude increases under tension and decreases under compression. When the coils were aligned perpendicular to the stress direction (line 602), the amplitude exhibited the opposite stress dependencies. However, the harmonic amplitude of each material varies significantly depending on the tempering temperature of the material, its composition, texture and hardness, so a technique is needed to distinguish harmonic amplitude variations due to material properties from harmonic amplitude changes due to actual mechanical damage.

Figure 7:
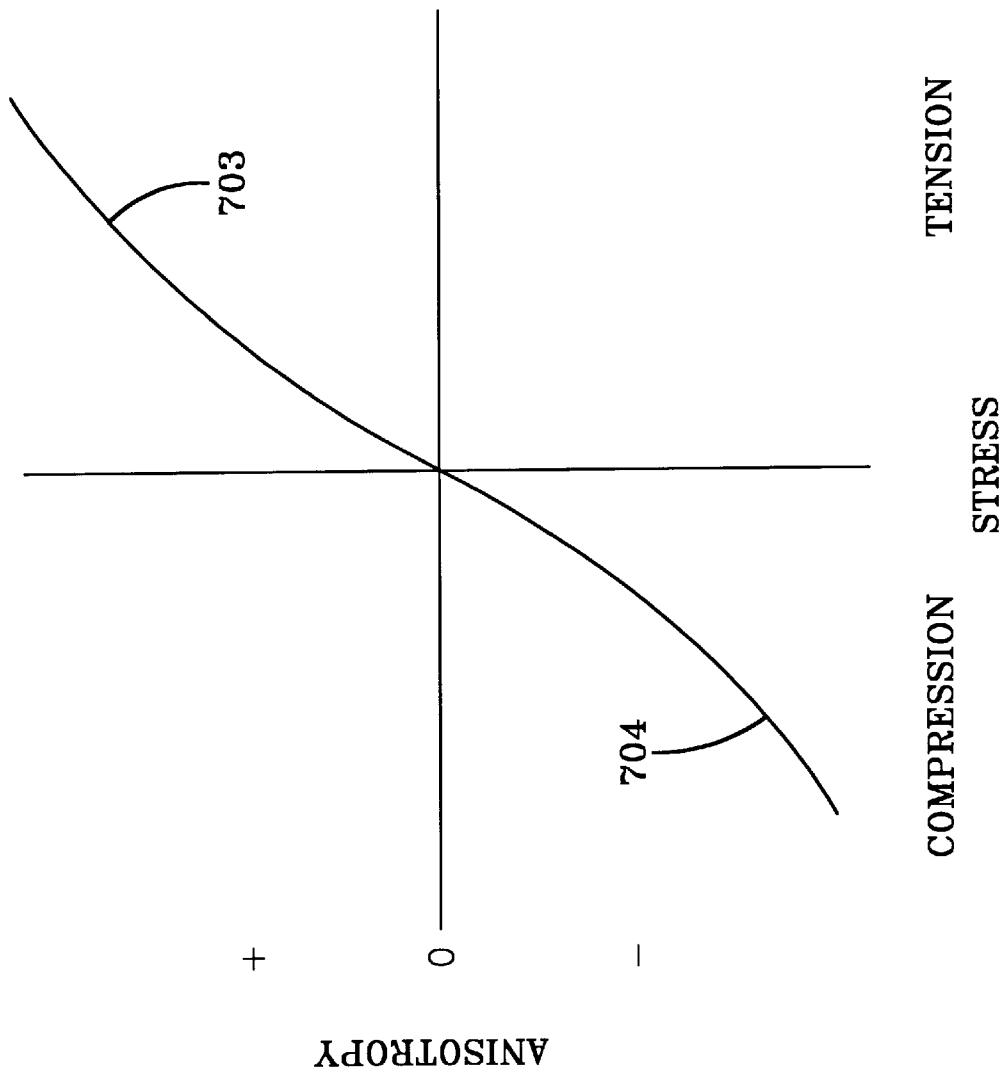
FIG. 7 shows the stress dependence of anisotropy for materials with positive magnetostriction.

To determine stress, a parameter which is sensitive to stress but insensitive to material properties is needed. Anisotropy in the harmonic signal amplitude is such a parameter because anisotropy is caused mainly by mechanical stresses. FIG. 7 shows the stress dependence of anisotropy for materials with positive magnetostriction. As shown in FIG. 6, for structural steels with positive magnetostriction, the harmonic amplitude increases with increasing tension and decreases with increasing compression when the applied magnetic field is parallel to the stress. When the applied field is perpendicular to the stress, the harmonic amplitude exhibits the opposite stress dependence. Because of the dependence of the harmonic amplitude on the relative orientation between the stress and the applied magnetic field, the harmonic amplitude exhibits anisotropy when the material is subjected to stress. An anisotropy parameter is defined as:

$$\text{Anisotropy} = (A_\| - A_\perp)/((A_\| + A_\perp)/2)$$

where $A_\|$ and $A_\perp$ are the harmonic amplitudes obtained with the applied magnetic field parallel and perpendicular to the stress direction, respectively and is used to determine the stress. As illustrated in FIG. 7, for materials with positive magnetostriction, anisotropy is positive under tension 703 and negative under compression 704, and increases in magnitude with increasing stress. Compared with the actual harmonic amplitude which changes significantly with variations in material properties not related to stress such as texture, hardness and heat treatment, the anisotropy is relatively insensitive to material property variations. This means that the anisotropy in magnetic properties is caused mainly by stress, so the anisotropy in the harmonic amplitude can be used as a stress indicator to differentiate stress from factors not related to stress (such as material texture, hardness and heat treatment). When stress induced anisotropy is used for stress determination, the accuracy of the technique improves.

Figure 8A:
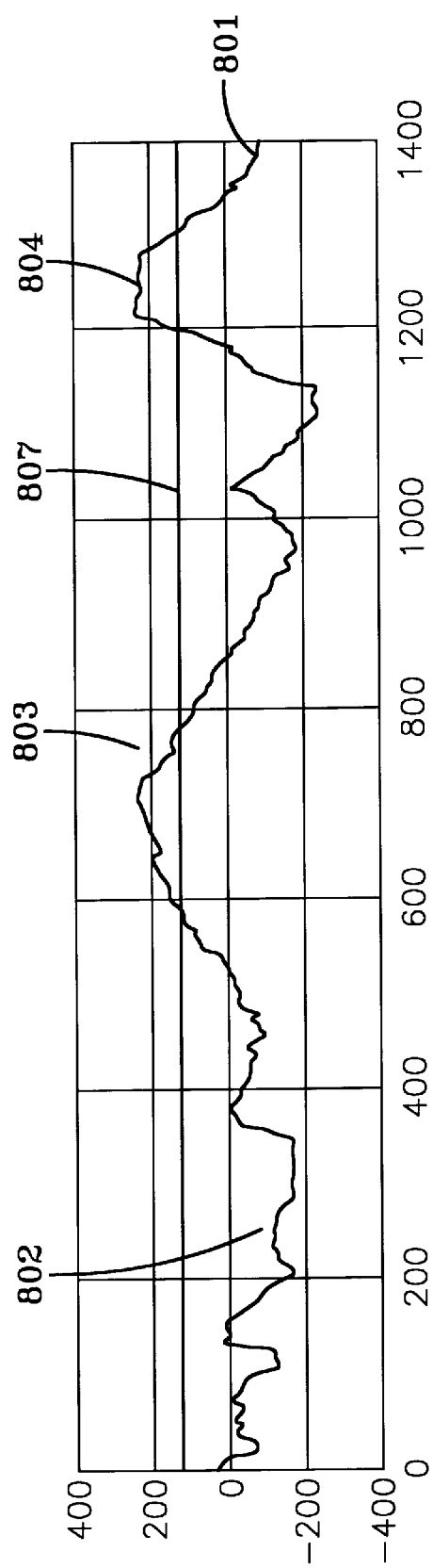
FIG. 8A shows a plot of the in-phase component of an NLH signal versus position on a pipeline as a pig with an NLH array of sensors (such as the embodiment depicted in FIG. 3) travels along the pipeline in accordance with the present inventive concept.
Figure 8B:
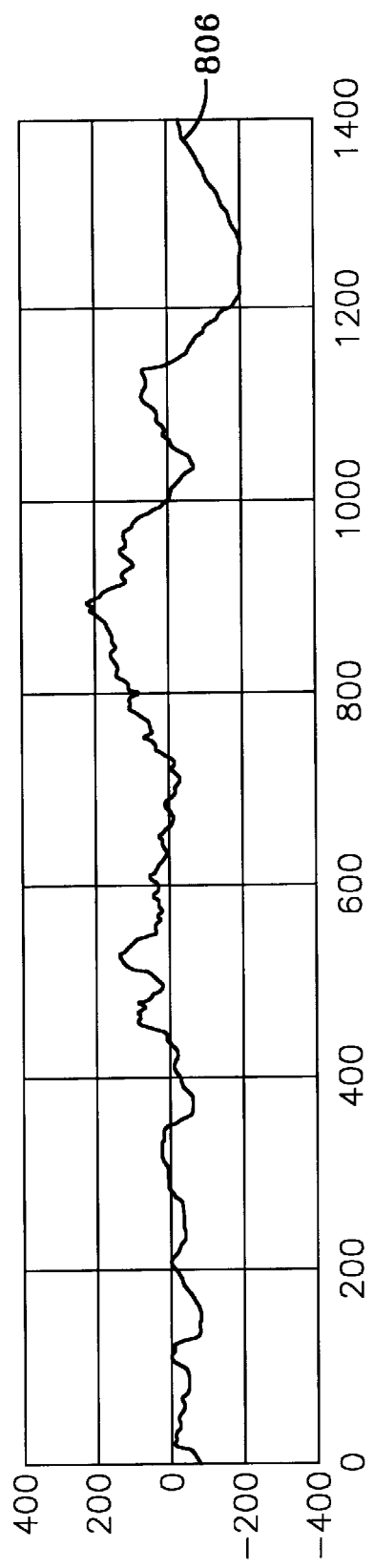
FIG. 8B shows a plot of the quadrature component of the NLH signal shown in FIG. 8A in accordance with the present inventive concept.

FIG. 8A shows a plot of the signal amplitude of an in-phase or real component of the NLH signal (208 in FIG. 2) versus its position on the pipeline as a pig with an NLH array of sensors (such as the embodiment depicted in FIG. 3) travels along the pipeline. The signal 801 shown in FIG. 8A is output from the lock-in amplifier (205 in FIG. 2). The in-phase component of the NLH signal 801 contains background noise signal components 802 as the NLH array passes over an undamaged region of the pipeline. The in-phase component of the NLH signal 801 contains mechanical damage signal components 803 as the NLH array passes over a damaged region of the pipeline. The in-phase component of the NLH signal 801 contains probe liftoff signal components 804 as the NLH array loses contact with the ferromagnetic portion of the pipeline as the array encounters nonmetallic material present in the pipeline such as scale or deposits on the pipe walls and the array "lifts off" the pipeline. The probe liftoff signal components 804 occur when the distance between the sensor arrays and the pipe wall change. Because the probe liftoff signal components 804 may be approximately the same amplitude as the mechanical damage signal components 803, there needs to be a way to distinguish the probe liftoff component of the signal 804 from the components of the signal indicating mechanical damage 804. This may be done by using the information contained in the in-phase 801 and quadrature components 806 of the NLH signal (208 and 209 in FIG. 2) as output from the lock-in amplifier (205 in FIG. 2) which is shown in FIG. 8B. The quadrature signal 806 is ninety degrees out-of-phase from the in-phase signal 801.

Figure 14:
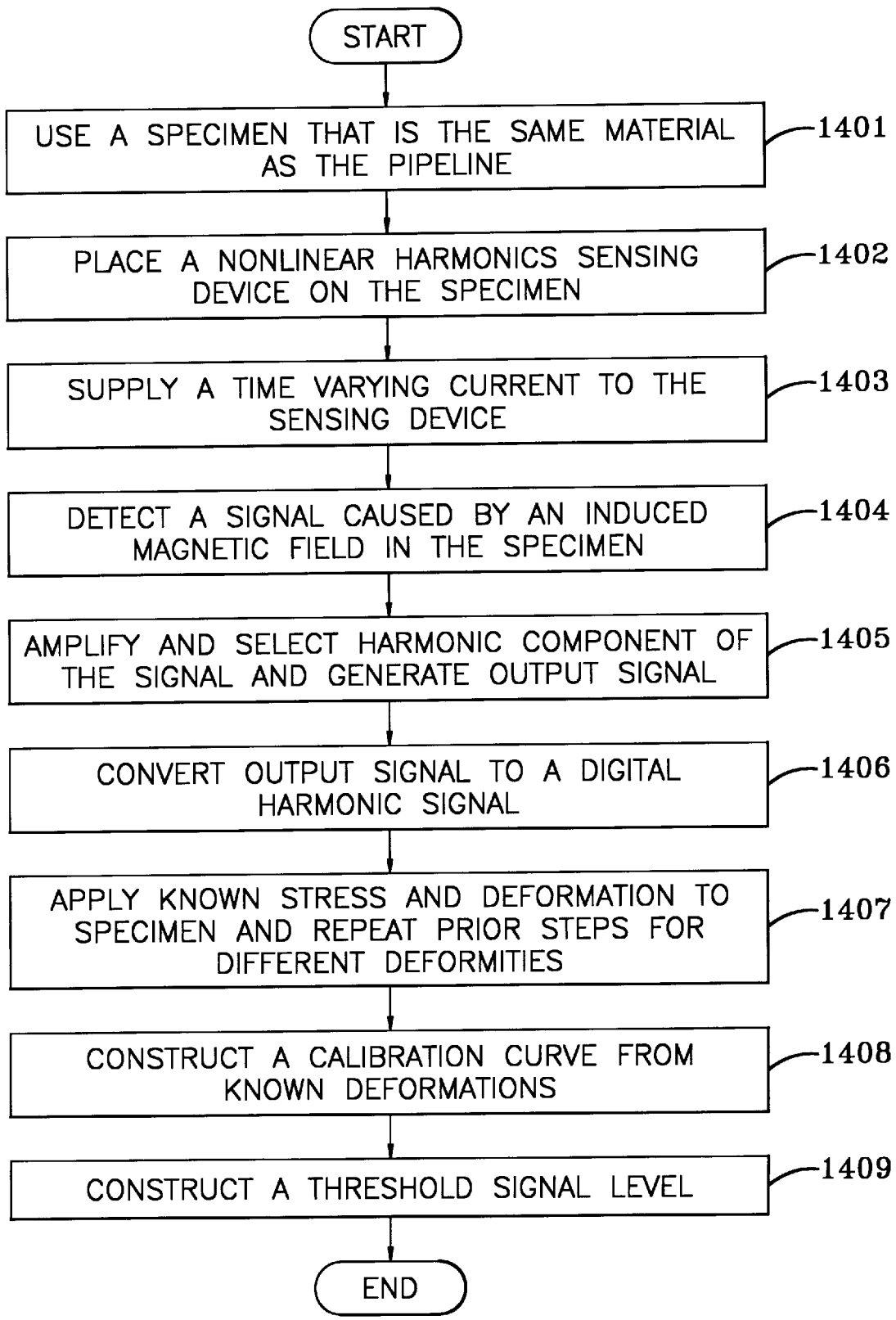
FIG. 14 is a flowchart of a method of determining a threshold level in accordance with the present inventive concept.
Figure 15:
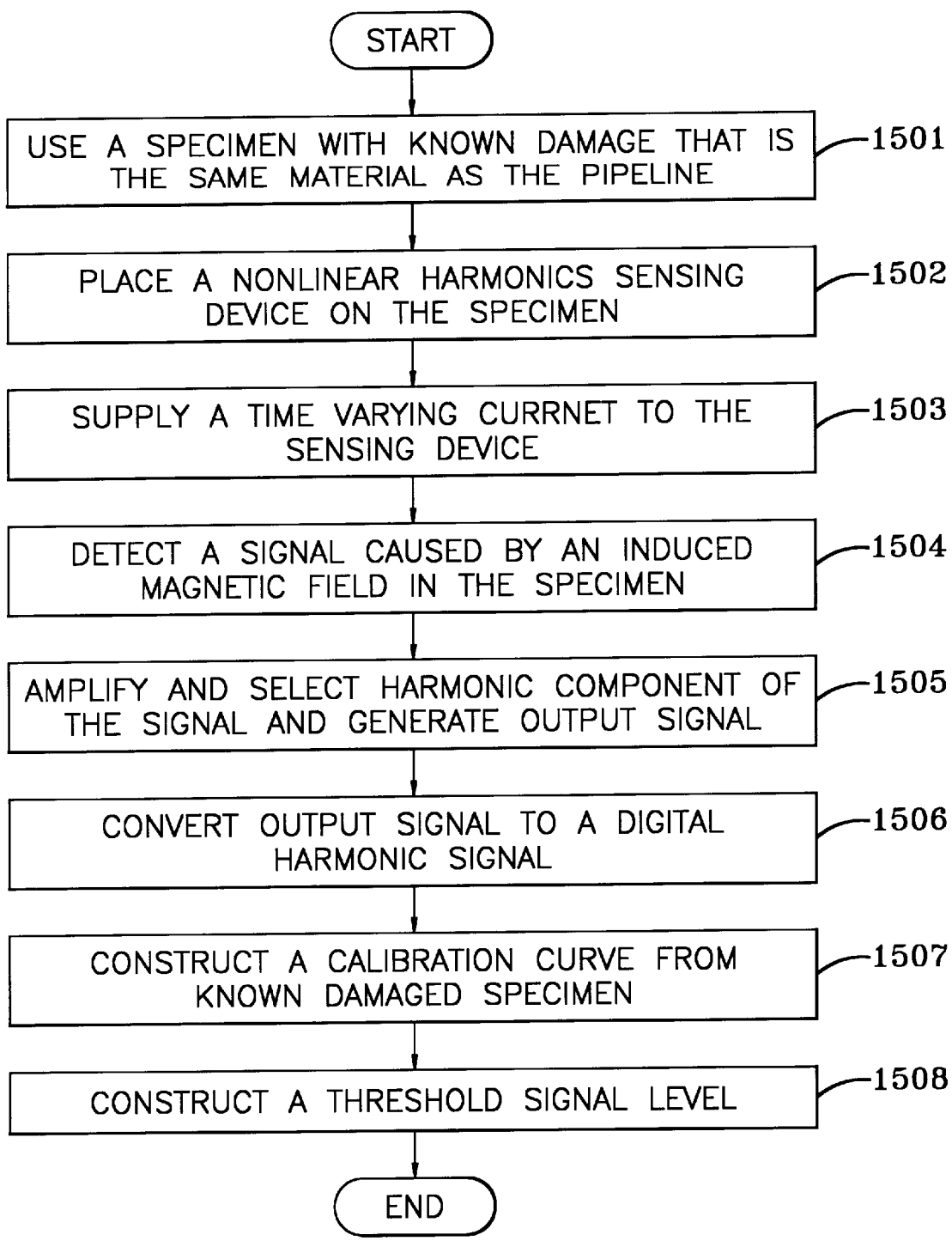
FIG. 15 is a flowchart of an alternative method of determining the threshold level signal in accordance with the present inventive concept.

A threshold level is represented by a threshold line 807 in FIG. 8A. Only areas of the NLH signal with an amplitude greater than the threshold line 807 are areas of the signal that are of interest for examining for mechanical damage. The threshold level is generally determined by calibrating the NLH system and the ferromagnetic material of the pipeline to determine a baseline and then determining a threshold level above which indicates an unacceptable level of mechanical damage. One method for calibrating the NLH system is to prepare a specimen of the same material as that to be tested and configuring it so that known amounts of stress and plastic deformation can be applied. An NLH probe would be placed on the specimen surface and NLH measurements recorded as a function of applied stress and plastic deformation. This information would be used to construct a calibration curve relating NLH readings to stress and plastic deformation. This curve would be applied to NLH measurements made on actual pipeline so that the stress and plastic deformation resulting from mechanical damage could be determined from the NLH readings. Another calibration method would be to prepare specimens of the same material as that to be tested and introducing known amounts of mechanical damage (dents and/or gouges). The amount of damage would bracket amounts known (from previous testing) to be detrimental to the integrity of the pipeline. NLH measurements may be made on these regions and an NLH threshold value established that may indicate detrimental amounts of damage. FIGS. 14 and 15 show alternative methods of determining the threshold level.

Figure 9A:
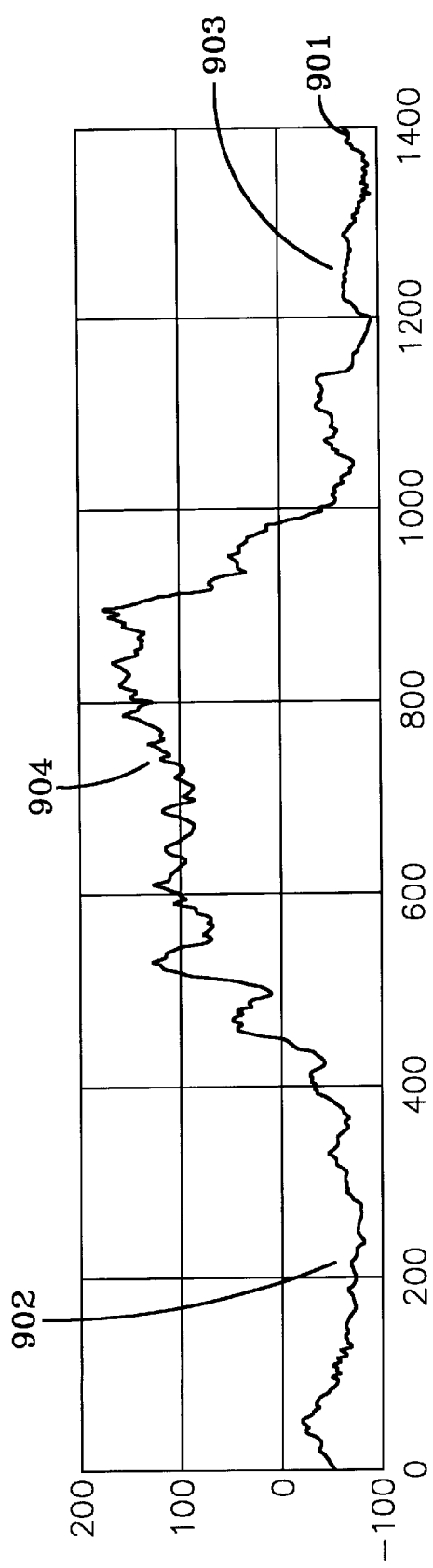
FIG. 9A shows a plot of an in-phase component of the NLH signal as shown in FIG. 8A after its phase has been shifted in accordance with the present inventive concept.
Figure 9B:
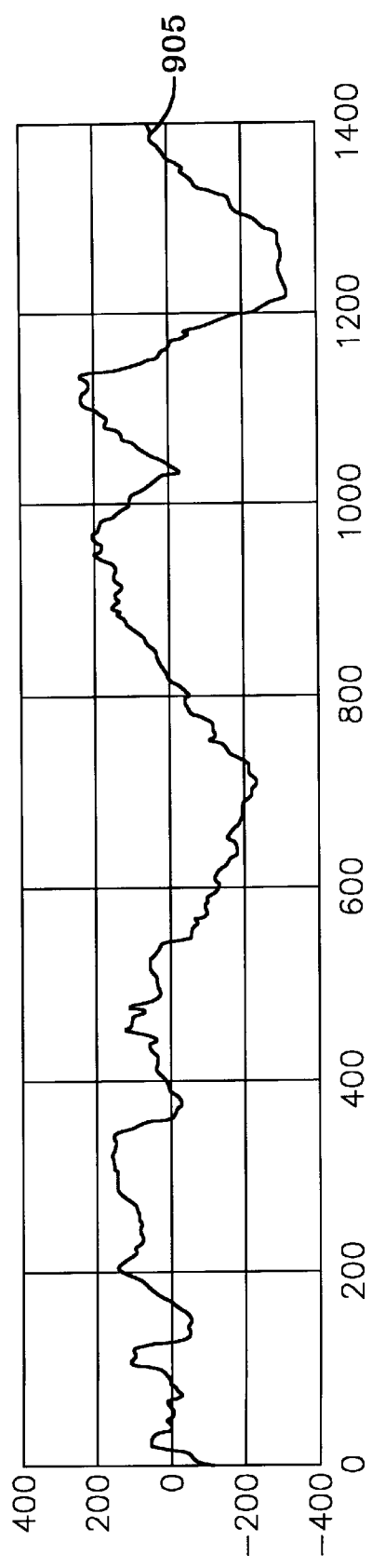
FIG. 9B shows a plot of the quadrature or imaginary component of the NLH signal after its phase has been shifted in accordance with the present inventive concept.

The probe liftoff signal components may be distinguished from mechanical damage signal components by shifting the relative phase as shown in FIGS. 9A and 9B. FIG. 9A shows a plot of an in-phase or real component of the NLH signal 901 as shown in FIG. 8A after its phase has been shifted, in this case by sixty three degrees. FIG. 9B shows a plot of the quadrature or imaginary component of the NLH signal 905 after its phase has been shifted by sixty three degrees. The phase shifting of the signal can occur onboard the pigging device by passing the phase reference signal (207 in FIG. 2) through a phase shift circuit. Alternatively, the phase shifting can occur during off-line computer analysis (405 in FIG. 4) using a mathematical phase shifting algorithm. The background noise signal components 902 (802 in FIG. 8A) have been effectively removed from the NLH signal 901. Similarly, the probe liftoff signal components 903 (804 in FIG. 8A) have also been effectively removed, leaving the mechanical damage signal components 904, indicating that an area of mechanical damage has occurred in an area within the pipeline. By shifting phase of the signal, the liftoff signal 903 is distinguished from the mechanical damage signal 904. An optimal phase shift can be determined by trial and error or by using an optimization program which phase shifts the signal in incremental amounts to determine the largest amplitude for the signal of interest and the smallest amplitude for the signal not of interest.

Figure 10:
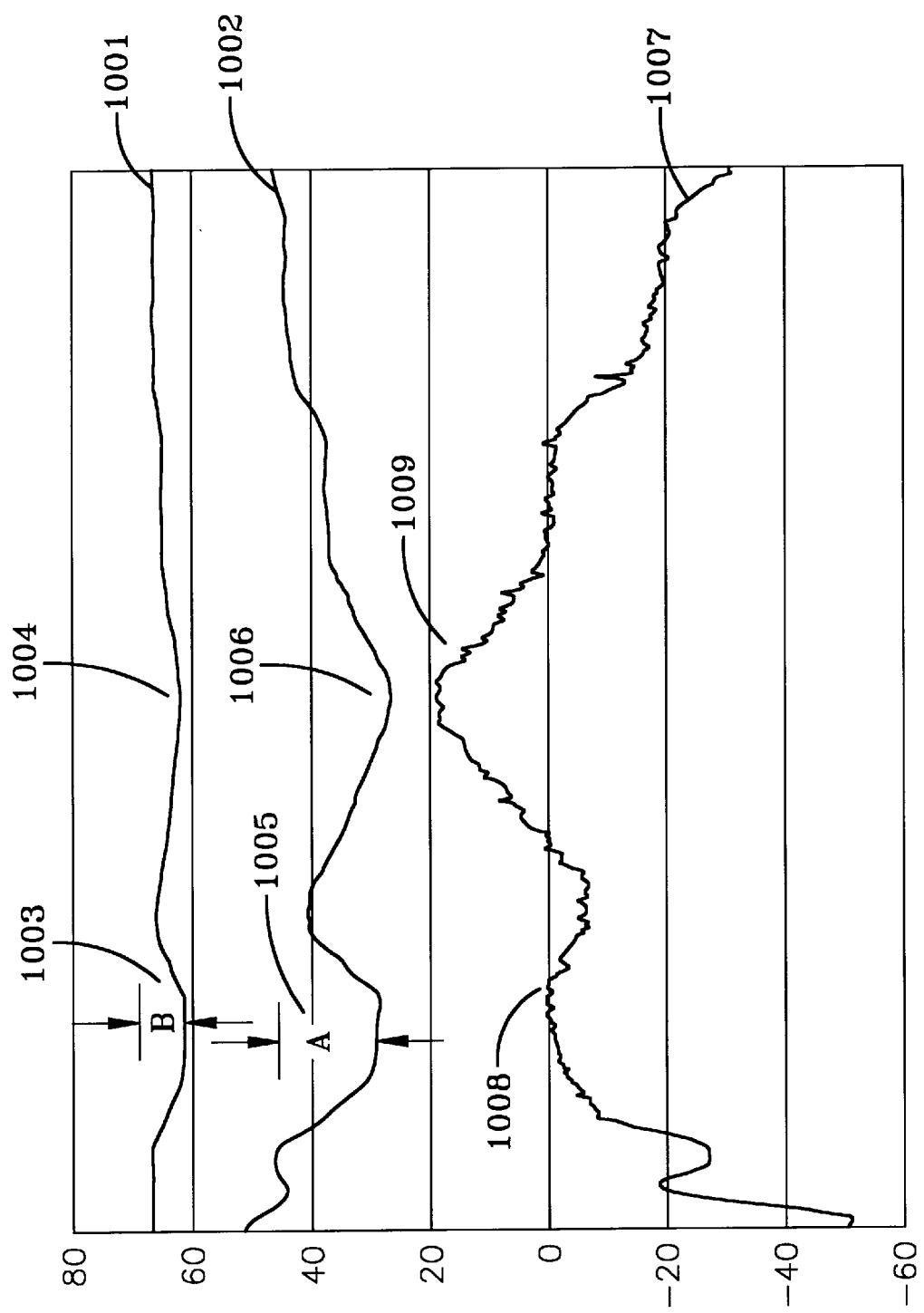
FIG. 10 shows a plot of the effect of scaling the harmonic value to the fundamental value in accordance with the present inventive concept.

Another way of distinguishing mechanical signal damage components from liftoff signal components is by scaling the harmonic value to the fundamental value and is shown in FIG. 10. This method accounts for variations in the fundamental frequency 1001 (also called the excitation frequency) that affect the amplitude of the measured harmonic signal 1002. If the fundamental frequency 1001 is reduced in amplitude as indicated by B 1003 while it is lifting off the pipeline, the amplitude of the resulting harmonic signal 1002 in the position of liftoff A 1005 is also reduced. If the fundamental frequency in the area of mechanical damage 1004 is reduced in amplitude, the amplitude of the resulting harmonic signal in that same position 1006 is correspondingly reduced. In this case, in the harmonic signal 1002, the liftoff signal components 1005 are not easily distinguishable from the mechanical damage signal components 1006. However, if the harmonic and fundamental frequencies are input to the following equation:

$$\text{Fundamental signal} - (B/A \times \text{harmonic signal})$$

where B is the amplitude of the fundamental frequency at a position on the pipeline and A is the amplitude of the harmonic signal at the same position on the pipeline, the result is the scaled signal 1007 showing most of the liftoff signal components 1008 removed and the mechanical damage components retained 1009. The equation above is one example of a method of scaling the signal. Other methods of scaling may be used.

The nonlinear harmonics technique can be used to measure near-surface stresses with sensing depth approximately equal to the skin depth of the applied magnetic field. Because the signal depth is a function of the frequency of the applied magnetic field, the depth of the sensing can be changed by varying the frequency. Therefore, the technique can be used to measure stress variations with depth. The use of NLH data obtained at different excitation frequencies can also be used to separate the mechanical damage flaw response from other undesired responses such as liftoff variations and localized magnetic property variations. This approach relies on the fact that the magnetic field produced by the NLH probe penetrates to different depths at different frequencies. The penetration depth is inversely proportional to the square root of the frequency and is calculated using a known skin depth equation. Provided that the depth profile of the two parameters to be distinguished is different, then independent information can be obtained by using multiple frequencies. For example, if the depth profile of the mechanical damage is different from that of the material property variations, then these two parameters will respond differently at different frequencies, and it is possible to separate their effects by using NLH data obtained at different frequencies. This is typically accomplished by determining a functional relationship between the mechanical damage signals and the degree of damage in the presence of the interfering signals. One approach is to perform a calibration where both the mechanical damage signals are measured for different degrees of damage, and the interfering signals from other parameters are also measured. A least squares fit is made to the data at different frequencies, but is fit only to the mechanical damage response without regard to the interfering signals. This same approach can be taken using the fundamental as one of the frequencies. The equation is typically a polynomial of a given degree. An example of a second degree fit using two frequencies is:

$$D = C_1 + C_2 R_1 + C_3 R_1^2 + C_4 X_1 + C_5 X_1^2 + C_6 R_2 + C_7 R_2^2 + C_8 X_2 + C_9 X_2^2$$

where D is the amount of damage, R1 and R2 are the in-phase components and X1 and X2 are the quadrature components, respectively of the two frequencies and C1 through C9 are weighting constants for the least squares fit.

FIG. 11 shows a typical NLH sensor probe configuration. The sensing coil 1101 and excitation coil 1102 are wrapped around a ferrite core 1103. In this embodiment the excitation coil 1102 is parallel to the ferromagnetic material 1104 and the magnetic field direction 1105 is also parallel to ferromagnetic material under test.

Figure 12:
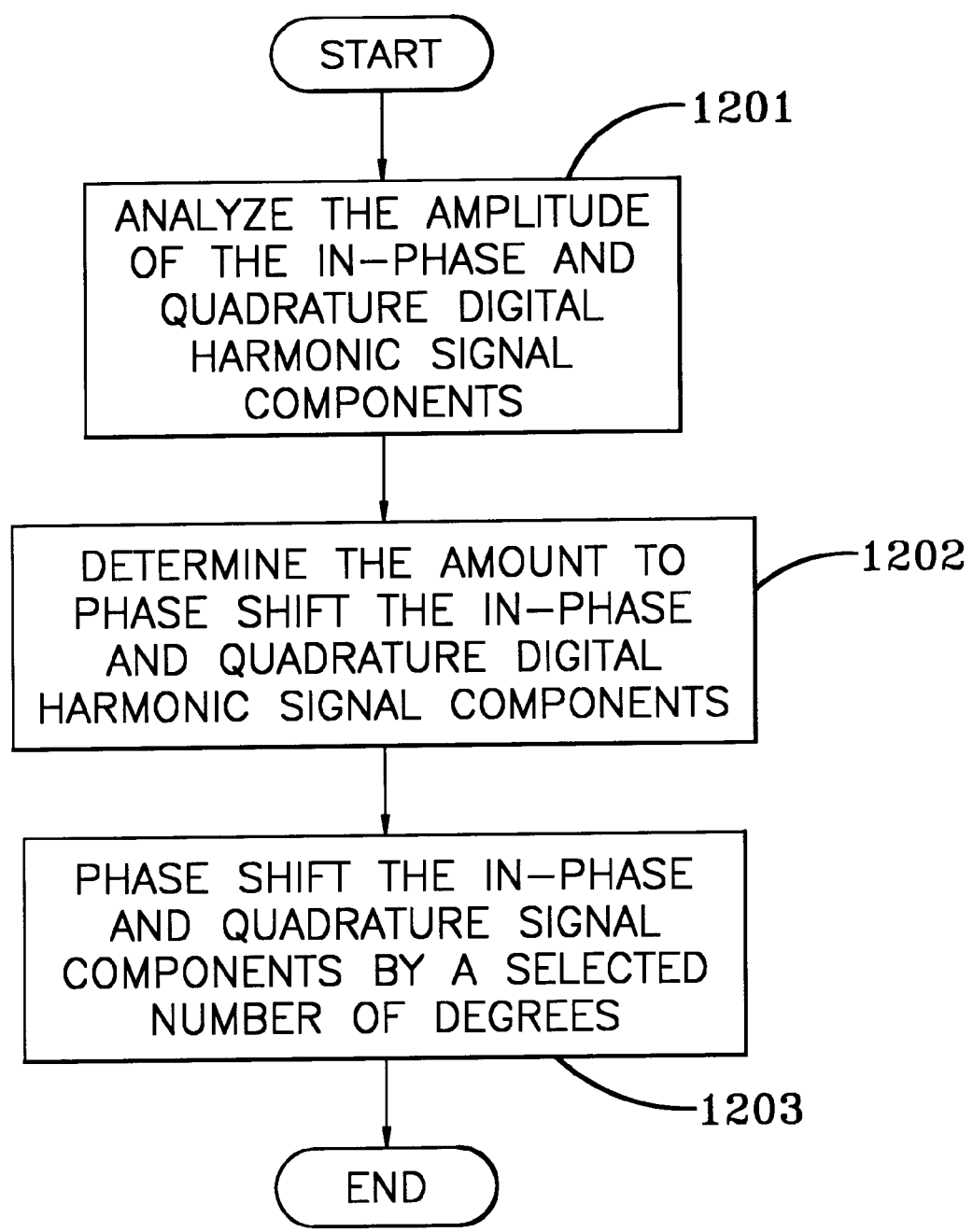
FIG. 12 is a flowchart of a method of analyzing the harmonic signal to detect areas of mechanical damage within a pipeline in accordance with the present inventive concept.

FIG. 12 is a flowchart of a method of analyzing the harmonic signal to detect areas of mechanical damage within a pipeline. The amplitude of the in-phase and quadrature digital harmonic signal components is analyzed 1201. The amount to phase shift the in-phase and quadrature digital harmonic signal components is determined 1202 and the in-phase and quadrature digital harmonic signal components are shifted by a selected number of degrees 1203 to remove the background signal and liftoff signal components with the resulting signal indicating the areas of mechanical damage along the pipeline.

Figure 13:
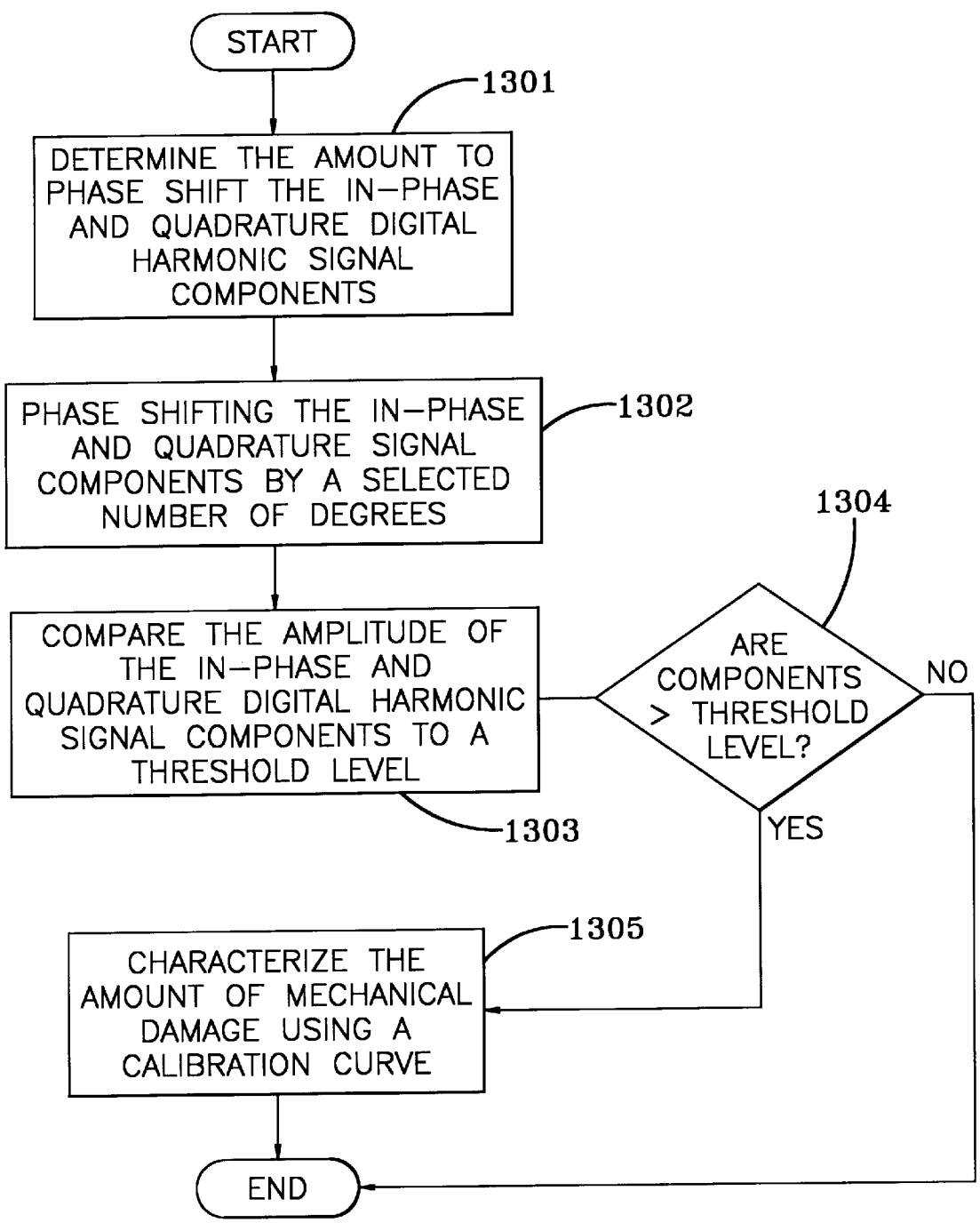
FIG. 13 is a flowchart of an alternative method of analyzing the harmonic signal to detect areas of mechanical damage within a pipeline in accordance with the present inventive concept.

FIG. 13 is a flowchart of an alternate method of analyzing the harmonic signal to detect areas of mechanical damage within a pipeline. The amount to phase shift the in-phase and quadrature digital harmonic signal components is determined 1301. The in-phase and quadrature digital harmonic signal components are shifted by a selected number of degrees 1302 to remove the background signal and liftoff signal components with the resulting signal indicating the areas of mechanical damage along the pipeline. The amplitude of the in-phase and quadrature digital harmonic signal components is compared to a threshold level 1303. If the components are greater than the threshold level 1304, the amount of mechanical damages is characterized using a calibration curve 1305. If the components are less than the threshold level 1304, the signal is not of interest and processing ends.

FIG. 14 is a flowchart of a method of determining a threshold level. Using a specimen of the same material as the pipeline 1401, a nonlinear harmonics sensing device is placed on the specimen 1402. A time varying current is supplied to the sensing device 1403. A signal caused by an induced magnetic field in the specimen is detected 1404. The harmonic component of the signal is amplified and selected and an output signal is generated 1405. The output signal is converted to a digital harmonic signal 1406. Known stress and plastic deformation are applied to the specimen and steps 1401 through 1406 are repeated for different deformations 1407. A calibration curve is constructed from known deformations 1408 and a threshold signal level is constructed 1409.

FIG. 15 is a flowchart of an alternative method of determining the threshold level signal. Using a specimen of the same material as the pipeline with known damage 1501, a nonlinear harmonics sensing device is placed on the specimen 1502. A time varying current is supplied to the sensing device 1503. A signal caused by an induced magnetic field in the specimen is detected 1504. The harmonic component of the signal is amplified and selected and an output signal is generated 1505. The output signal is converted to a digital harmonic signal 1506. A calibration curve is constructed from the known damaged specimen 1507 and a threshold signal level is constructed 1508.

Figure 16:
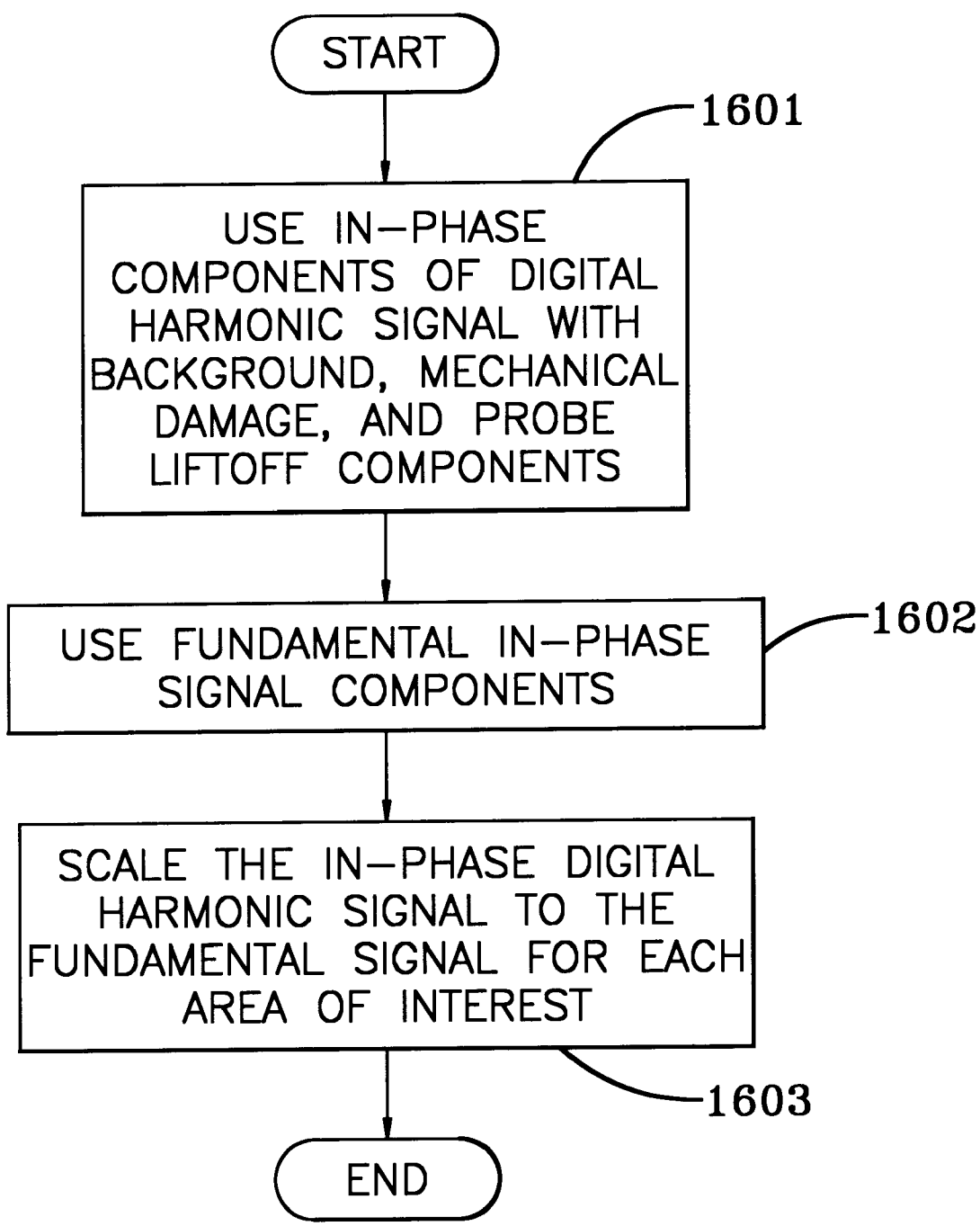
FIG. 16 is a flowchart of an alternative method of analyzing the amplitude of the digital harmonic signal to detect areas of mechanical damage within a pipeline in accordance with the present inventive concept.

FIG. 16 is a method of analyzing the amplitude of the digital harmonic signal to detect areas of mechanical damage within a pipeline. Using the in-phase components of the digital harmonic signal with background, mechanical damage and probe liftoff signal components 1601 and the fundamental in-phase signal components 1602, the in-phase digital harmonic signal is scaled to the in-phase fundamental signal for each area of interest 1603 with the resulting signal having substantially all the liftoff signal components removed and substantially all the mechanical damage signal components retained.

What is claimed is:

1. A system for nondestructive testing utilizing nonlinear harmonic techniques to determine mechanical damage within ferromagnetic material of a pipeline, comprising:
   a. means for supplying a time varying current at a fundamental frequency to a nonlinear harmonic sensor and for outputting a phase reference signal contained within a pigging device for passing through a pipeline;
   b. the nonlinear harmonic sensor attached to a pigging device for passage through a pipeline comprising:
      i. an excitation coil for generating a magnetic field within a pipeline when supplied with the time varying current as the pigging device passes through the pipeline;
      ii. a sensing coil for detecting a signal caused by induced magnetic field in the pipeline;
   c. means for amplifying and selecting a portion of the signal of step b. ii. that represents a harmonic frequency component of the signal and generating an output signal using the phase reference signal;
   d. means connected to the pigging device for converting the output signal to a digital harmonic signal;
   e. means connected to the pigging device for storing the digital harmonic signal; and
   f. computer means for removing probe liftoff signal components and analyzing the digital harmonic signal to detect areas of stress and plastic deformation within the pipe.

2. A system according to claim 1, wherein the computer means for analyzing the digital harmonic signal is contained within the pigging device.

3. A system according to claim 1, wherein the computer means for analyzing the digital harmonic signal is external to the pigging device.

4. A system according to claim 1, wherein the harmonic signal is at a third harmonic frequency of the fundamental frequency.

5. A system according to claim 1, wherein the means for supplying the time varying current at the fundamental frequency to a nonlinear harmonic sensor and for outputting the phase reference signal is a signal generator and power amplifier.

6. A system according to claim 1, wherein:
   a. the digital harmonic signal stored for analysis comprises an in-phase signal component an a quadrature signal component; and
   b. the phase reference signal component is output to an amplifier which generates and in-phase and quadrature reference signal component.

7. A system according to claim 1, wherein the fundamental frequency is a selected frequency in the range of between about 100 Hz to about 100 kHz.

8. A system according to claim 1, wherein the means for amplifying and selecting the portion of the signal that represents the harmonic frequency component of the signal and generating a harmonic signal using the phase reference signal further comprises:
   a. filter means for filtering the output signal to remove frequencies other than harmonic frequencies; and
   b. means for frequency multiplying the phase reference signal and passing the multiplied phase reference signal to a lock-in amplifier that uses the multiplied phase reference signal and filtered harmonic signal to generate a complex harmonic signal with in-phase and quadrature signal components.

9. A system according to claim 1, wherein:
   a. the pigging device comprises a pressure vessel; and
   b. the nonlinear harmonic sensor comprises a plurality of nonlinear harmonics sensing devices attached to the pressure vessel to form sensor arrays.

10. A system according to claim 9, wherein the nonlinear harmonics sensing devices extend outward from spring-loaded suspensions attached to the pressure vessel and the sensing devices rest against the inner surface of the pipeline.

11. A system according to claim 10, wherein the nonlinear harmonic sensors are attached to the pressure vessel and oriented with the magnetization direction parallel with a pipeline axis.

12. A system according to claim 10, wherein the nonlinear harmonic sensors are attached to the pressure vessel and oriented with the magnetization direction perpendicular to a pipeline axis.

13. A system according to claim 10, wherein a selected number of the nonlinear harmonic sensing devices are attached to the pressure vessel and oriented with the magnetization direction parallel with a pipeline axis and the remaining number of the nonlinear harmonic sensing devices are attached to the pressure vessel and oriented with the magnetization direction perpendicular to the pipeline axis.

14. A system according to claim 10, wherein the pigging device is capable of traveling through the pipeline at a speed of about ten meters per second.

15. A system for nondestructive testing utilizing nonlinear harmonics techniques to determine mechanical damage within the ferromagnetic material of a pipeline, comprising:
   a. means for generating a time varying magnetic field within a pipeline and outputting a phase reference signal, contained within a pigging device for passage through a pipeline;
   b. means for sensing a signal generated by the induced magnetic field in the pipeline, mounted on the pigging device;
   c. means for amplifying the signal and detecting a harmonic frequency component of the signal;
   d. means for storing the harmonic frequency component; and
   e. computer means for removing probe liftoff signal components and analyzing an amplitude of the harmonic frequency component to detect areas of stress and plastic deformation within the pipeline.

16. A method for nondestructive testing utilizing nonlinear harmonics techniques to determine mechanical damage within ferromagnetic material of a pipeline, comprising the steps of:
   a. supplying a time varying current at a fundamental frequency to an excitation coil for generating a magnetic field within a pipeline and outputting a fundamental phase reference signal, within a pigging device for passing through a pipeline;
   b. detecting a signal caused by induced magnetic field in the pipeline using a sensing coil attached to the pigging device;
   c. amplifying and selecting a portion of the signal of step b that represents a harmonic frequency component of the signal and outputting an output signal;
   d. converting the output signal to a digital harmonic signal;
   e. storing the digital harmonic signal and phase reference signal within the pigging device; and
   f. removing probe liftoff signal components and analyzing the amplitude of the digital harmonic signal to detect areas of stress and plastic deformation within the pipeline using a computer program.

17. A method for nondestructive testing utilizing nonlinear harmonics techniques to determine mechanical damage within ferromagnetic material of a pipeline, comprising the steps of:
   a. supplying a time varying current at a fundamental frequency to an excitation coil for generating a magnetic field within a pipeline and outputting a fundamental phase reference signal, within a pigging device for passing through a pipeline;
   b. detecting a signal caused by the induced magnetic field in the pipeline using a sensing coil attached to the pigging device;
   c. amplifying and selecting a portion of the signal of step b. that represents a harmonic frequency component of the signal and outputting an output signal;
   d. converting the output signal to a digital harmonic signal;
   e. outputting the phase reference signal to an amplifier which generates an in-phase and quadrature fundamental signal component;
   f. storing the digital harmonic signal and the phase reference signal within the pigging device, the digital harmonic signal stored comprises an in-phase signal component and a quadrature signal component; and
   g. removing probe liftoff signal components and analyzing the amplitude of the digital harmonic signal to detect areas of stress and plastic deformation within the pipeline using a computer program.

18. A method according to claim 17, in the amplifying and selecting step, further comprising the steps of:
   a. filtering the output signal to remove frequencies other than harmonic frequencies; and
   b. frequency multiplying the phase reference signal and passing the multiplied phase reference signal to a lock-in amplifier that uses the multiplied phase reference signal and filtered harmonic signal to generate a complex harmonic signal with in-phase and quadrature signal components.

19. A method according to claim 16, wherein:
   a. the pigging device comprises a pressure vessel; and
   b. the nonlinear harmonic sensor comprises a plurality of nonlinear harmonics sensing devices attached to the pressure vessel to form sensor arrays.

20. A method according to claim 19, wherein the nonlinear harmonics sensing devices extend outward from spring-loaded suspensions attached to the pressure vessel and the sensing devices rest against the inner surface of the pipeline.

21. A method according to claim 16, wherein the harmonic signal is at a third harmonic frequency of the fundamental frequency.

22. A method, according to claim 19, further comprising the step of attaching a plurality of nonlinear harmonic sensing devices to a pressure vessel of the pigging device to form sensor arrays.

23. A method according to claim 22, further comprising the step of attaching the nonlinear harmonic sensing devices, oriented parallel with a pipeline axis, to the pressure vessel.

24. A method according to claim 22, further comprising the step of attaching the nonlinear harmonic sensing devices, oriented perpendicular to the pipeline axis, to the pressure vessel.

25. A method according to claim 22, further comprising the steps of attaching a plurality of the nonlinear harmonic sensing devices, oriented parallel with the pipeline axis, to the pressure vessel and attaching the remaining nonlinear harmonic sensing devices, oriented perpendicular to the pipeline axis, to the pressure vessel.

26. A method according to claim 17, wherein the analyzing the harmonic signal amplitude to detect areas of mechanical damage within the pipeline using a computer program step, further comprises:
 a. analyzing the amplitude of the in-phase and quadrature digital harmonic signal components which contain background signal components, mechanical damage signal components and probe liftoff signal components;
 b. determining the amount to phase shift the in-phase and quadrature digital harmonic signal components to remove the background signal and liftoff signal components; and
 c. phase shifting the in-phase and quadrature signal components by a selected number of degrees to remove the background signal and liftoff signal components, with the resulting signal indicating the areas of mechanical damage along the pipeline.

27. A method according to claim 17, wherein the analyzing the harmonic signal amplitude to detect areas of mechanical damage within the pipeline using a computer program step, further comprises:
 a. determining the amount to phase shift the in-phase and quadrature digital harmonic signal components to remove the background signal and liftoff signal components;
 b. phase shifting the in-phase and quadrature signal components by a selected number of degrees to remove the background signal and liftoff signal components;
 c. comparing the amplitude of the in-phase and quadrature digital harmonic signal components to an amplitude of a threshold signal level; and
 d. characterizing the amount of mechanical damage using a calibration curve if the amplitude of the in-phase and quadrature digital harmonic signal is greater than the amplitude of a threshold level.

28. A method according to claim 27, further comprising determining the threshold level signal comprising:
 a. using a specimen that is the same material as the pipeline;
 b. placing a nonlinear harmonics sensing device on the specimen;
 c. supplying a time varying current at a given frequency to the nonlinear harmonics sensing device and outputting a fundamental phase reference signal;
 d. detecting a signal caused by induced magnetic field in the specimen;
 e. amplifying and selecting a portion of the signal of step d that represents a harmonic frequency component of the signal and generating an output signal;
 f. converting the output signal to a digital harmonic signal;
 g. applying a known amount of stress and plastic deformation to the specimen and repeating steps a through f for a fixed number of known stresses;
 h. constructing the calibration curve by plotting the digital harmonic signal corresponding to each known stress; and
 i. constructing a threshold signal level.

29. A method according to claim 27, further comprising determining the threshold level signal comprising:
 a. using a specimen that is the same material as the pipeline with known amounts of mechanical damage;
 b. placing a nonlinear harmonics sensing device on the specimen;
 c. supplying a time varying current at a given frequency to the nonlinear harmonics sensing device and outputting a fundamental phase reference signal;
 d. detecting a signal caused by induced magnetic field in the specimen;
 e. amplifying and selecting a portion of the signal of step d that represents a harmonic frequency component of the signal and generating an output signal;
 f. converting the output signal to a digital harmonic signal;
 g. constructing the calibration curve by plotting the digital harmonic signal corresponding to the mechanical damage; and
 h. constructing a threshold signal level.

30. A method according to claim 27, wherein the number of degrees of phase shifting is determined by using an optimization software program which phase shifts the signal in incremental amounts to determine a largest amplitude for a signal of interest and a smallest amplitude for a signal not of interest.

31. A method according to claim 17, wherein in analyzing the amplitude of the digital harmonic signal to detect areas of mechanical damage within the pipeline using a computer program step, further comprising the steps of:
 a. using the amplitude of the digital harmonic signal in-phase signal components which contain background signal components, mechanical damage signal components and probe liftoff signal components;
 b. using the amplitude of the fundamental in-phase signal components;
 c. scaling the digital harmonic signal to the fundamental in-phase signal, for each area of interest, comprising taking the reduction in amplitude of the fundamental in-phase signal divided by the reduction in amplitude for the digital harmonic signal, multiplied by the digital harmonic signal amplitude, then subtracting that result from the fundamental in-phase signal amplitude to generate a resulting signal, the resulting signal having substantially all the liftoff signal components removed and substantially all the mechanical damage signal components retained such that areas of mechanical damage along the pipeline are indicated by changes in amplitude of the resulting signal.

32. A method according to claim 17, in the analyzing the harmonic signal amplitude to detect areas of mechanical damage within the pipeline using a computer program step, further comprising the step of calculating anisotropy in the digital harmonic signal amplitude to detect areas of mechanical damage.

33. A method for nondestructive testing utilizing nonlinear harmonics techniques to determine mechanical damage within ferromagnetic material of a pipeline, comprising the steps of:

a. supplying a time varying current at plurality of fundamental frequencies to an excitation coil for generating a magnetic field within a pipeline and outputting a fundamental phase reference signal, within a pigging device for passing through a pipeline;

b. detecting a signal caused by induced magnetic field in the pipeline using a sensing coil attached to the pigging device;

c. amplifying and selecting a portion of the signal of step b that represents a plurality of harmonic frequency components of the signal and outputting an output signal;

d. converting the output signal containing a plurality of harmonic frequency components to a digital harmonic signal which comprises an in-phase signal component and a quadrature signal component;

e. outputting the phase reference signal component to an amplifier which generates an in-phase and quadrature fundamental signal component;

f. storing the digital harmonic signal and phase reference signal within the pigging device; and g. removing probe liftoff signal components and comparing amplitudes of the digital harmonic signals at a plurality of harmonic frequencies to detect areas of stress and plastic deformation within the pipeline.

34. A method according to claim 17, further comprising:

a. performing the method of claim 17, steps a through f for a first fundamental frequency, filtering the first fundamental frequency components from the harmonic signal and frequency multiplying the phase reference signal and passing the multiplied phase reference signal to a lock-in amplifier that uses the multiplied phase reference signal and filtered harmonic signal to generate a first complex harmonic signal with in-phase and quadrature signal components;

b. repeating the method of claim 17, steps a through f for a second fundamental frequency, filtering the first fundamental frequency components from the harmonic signal and frequency multiplying the phase reference signal and passing the multiplied phase reference signal to a lock-in amplifier that uses the multiplied phase reference signal and filtered harmonic signal to generate a second complex harmonic signal with in-phase and quadrature signal components;

c. comparing the amplitudes of the first and second complex harmonic signals with in-phase and quadrature signal components which contain background signal components, mechanical damage signal components and probe liftoff signal components and generating a signal having substantially all the liftoff signal components removed and substantially all the mechanical damage signal components retained such that areas of mechanical damage along the pipeline are indicated by changes in amplitude of the resulting signal.

* * * * *